United States Patent [19]

Rogasch et al.

[11] Patent Number: 4,776,694

[45] Date of Patent: Oct. 11, 1988

[54] BURNER ASSEMBLY FOR ATOMIC ABSORPTION SPECTROMETER

[75] Inventors: Klaus P. Rogasch, Hofmannweg; Rolf Tamm, Am Fohrenbuhl, both of Fed. Rep. of Germany

[73] Assignee: Bodenseewerk Perkin-Elmer & Co., GmbH, Uberlingen, Fed. Rep. of Germany

[21] Appl. No.: 932,957

[22] Filed: Nov. 19, 1986

[30] Foreign Application Priority Data

Nov. 21, 1985 [DE] Fed. Rep. of Germany ....... 3541107

[51] Int. Cl.$^4$ ............................................. G01N 21/72
[52] U.S. Cl. ................................................. 356/315
[58] Field of Search .................... 356/315, 417; 431/4, 431/126, 79, 191

[56] References Cited

U.S. PATENT DOCUMENTS

| 3,523,748 | 8/1970 | Chisholm et al. ................... 356/315 |
| 3,531,203 | 9/1970 | Isreeli et al. ......................... 356/315 |
| 3,583,844 | 6/1971 | Smith, Jr. .............................. 356/87 |
| 3,586,441 | 6/1971 | Smith et al. .......................... 356/315 |
| 3,600,571 | 8/1971 | Chisholm et al. ................. 240/41.35 |

Primary Examiner—F. L. Evans
Attorney, Agent, or Firm—Francis L. Masselle; Ronald G. Cummings; Edwin T. Grimes

[57] ABSTRACT

A burner assembly for an atomic absorption spectrometer having carrier (20) fixed to the burner head (14) and mounting a flame sensor (96) and an ignition device (16) so as to permit a single alignment of the flame sensor (18) and the ignition device (16) relative to the burner head (14) and subsequent movement or adjustment of the burner relative to the housing without changing the mutual positions of the ignition device (16) and the flame sensor (18) and while the flame is burning.

22 Claims, 2 Drawing Sheets

BURNER ASSEMBLY FOR ATOMIC ABSORPTION SPECTROMETER

BACKGROUND AND SUMMARY OF THE INVENTION

The present invention relates to an atomic absorption spectrometer and more particularly to a burner assembly for such a spectrometer.

In atomic absorption spectroscopy, a measuring light beam comprising a line spectrum with the resonant wavelength of a looked-for element is emitted by a light source. The measuring light beam is passed through a "cloud of atoms" in which the element of a sample is present in an atomic state. The measuring light beam is specifically absorbed by the atoms of the looked-for element since the resonant wavelength coincides with the line spectrum of the measuring lightbeam. The measuring light beam on the other hand is practically not affected by the atoms of the other elements of the sample since their resonant wavelengths do not coincide with those of the measuring light beam. Therefore, the measuring light beam undergoes an absorption which is indicative of the proportion of the looked-for element in the sample. with reproducible generation of the cloud of atoms and appropriate calibration, atomic absorption spectroscopy is a highly sensitive and quantitatively accurate analyzing method.

In many cases of application, the atomization of a sample is effected by means of a flame so that the individual elements are present in an atomic state in a cloud of atoms. Sample fluid is sprayed into a mixing chamber by a nebulizer. Fuel gas and oxidizing agent are introduced into the mixing chamber and mixed. The generated mist of sample substance is entrained into the flame whereby decomposition and atomization of the sample substance takes place in the flame.

It is often necessary to adjust or shift the burner relative to the measuring light beam as for example in order to vary the length of the path of the measuring light beam through the flame. It has also been proposed to arrange the burner to be optionally movable out of the path of the light beam for measurments without a flame with a single-beam instrument in order to determine the base line to compensate for variations of the lamp intensity and/or sensitivity of the detector. Such an assembly is shown in the copending commonly-assigned application of Huber et al., U.S. Ser. No. 893,766 entitled Atomic Absorption Spectrometer filed Aug. 6, 1986 which is incorporated by reference herein in its entirety.

Further, it is necessary to ignite the flame on the burner and an advantageous ignition device is shown in the copending commonly-assigned application of Huber et al. U.S. Ser. No. 905,807, entitled Device and Technique for Lighting a Flame in an Atomic Absorption Spectrophotometer filed Sept. 10, 1986 which is incorporated by reference herein in its entirety. The ignition device includes a tube with a first end cut off at an angle pivotable above the burner head of the burner of an atomic absorption spectrometer. Gas emerging from the burner is diverted through the tube from the first end to a second end where a glow filament is arranged. The diverted gas is ignited and flashes back to the burner whereby the burner flame is ignited. After the flame has been ignited the tube is rotated out of the area of the burner head by a rotary magnet.

For safety reasons, it is furthermore necessary to monitor the burning of the flame. The fuel gas supply is interrupted if no flame is generated by the ignition procedure or if the flame extinguishes during operation. The release of unburned fuel gas presents a dangerous situation and therefore the flame sensor monitoring the flame must be highly reliable. This high reliability has to be ensured throughout an extended period of time and also under disadvantageous environmental conditions such as heat, corrosive mists and frequent moving. In known apparatus, the UV-radiation of the flame is detected by a photo cell. Such a circuit however requires a high supply voltage and provides very high impedance signals. The circuit is also susceptible to electromagnetic pick-up. Chip-integrated thermo-columns are also utilized as radiation detectors and have small housing dimensions, low inner impedances, high signal levels and small time constants.

It is an object of the present invention to provide a new and improved burner assembly for an atomic absorption spectrometer.

Another object of the invention is to provide a burner assembly having an integrally mounted displaceable burner head, a burner ignition, and flame sensor.

Another object of the invention is to provide a burner assembly which allows displacement of the burner head without readjustment and realignment of the ignition device and/or flame sensor.

A further object of the invention is to provide a new and improved flame sensor assembly for use with such a burner assembly.

A still further object of the invention is to provide a flame sensor assembly which is economical in construction and reliable and durable in use.

Other objects will be in part obvious and in part pointed out more in detail hereinafter.

It has been found that the foregoing and related objects may be attained in a burner assembly for an atomic absorption spectrometer defining a predetermined optical path for a measuring light beam which includes burner means for generating a flame for atomization having a burner head and being moveably mounted for selective movement relative to the predetermined optical path. A support carrier is securely connected to the burner and mounts an ignition assembly for igniting a flame on the burner head and a sensor for monitoring the flame. The sensor is positioned in predetermined alignment with the burner and securely mounted to the carrier so as to maintain alignment after selective movement of the burner. The ignition is also positioned in predetermined operational alignment with the burner and is securely mounted to the carrier as to maintain this alignment after selective movement of the burner. In one embodiment of the invention, the burner is movably mounted for selective movement between first and second positions with the flame being within the optical path when the burner is in the first position and without the optical path when the burner is in the second position for determining a base line.

Thus, the ignition device and flame sensor are mounted to the carrier which is connected to the burner head. Therefore, displacement of the burner can be made without, for example, the flame sensor becoming inoperative or having to be adjusted anew. Additionally, it is also possible to displace the burner head with a burning flame or to move it out of the path of the rays of the measuring light beam.

DESCRIPTION OF THE PREFERRED EMBODIMENT

Figure 1:
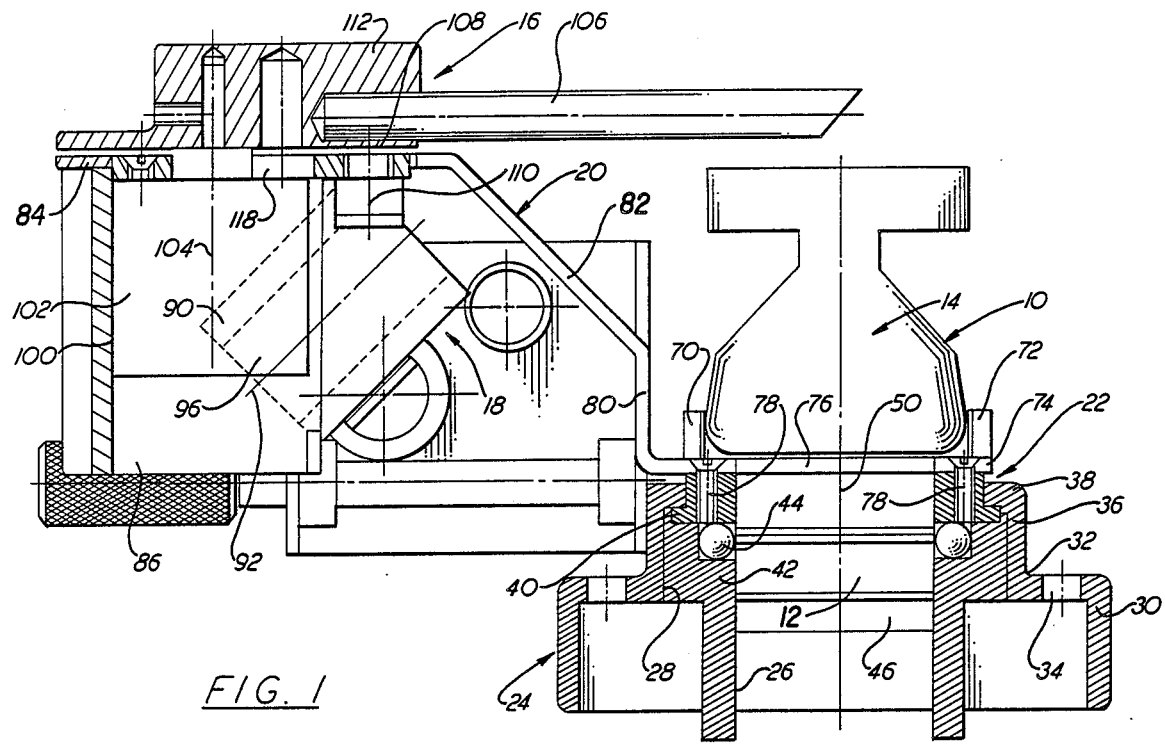
FIG. 1 is a side-elevation diagrammatic view, partially in section, of the burner assembly of the present invention.

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the burner assembly generally comprises a burner 10 with a mixing chamber 12 and a burner head 14 attached thereto, an ignition device 16 for lighting the burner 10, and a flame sensor 18 for monitoring the flame burning on the burner head 14. The ignition device 16 and the flame sensor 18 are mounted on a support plate or carrier 20 fixedly connected to the burner head 14. The burner assembly may include the movable support assembly as shown in the commonly assigned Huber et al., U.S. patent application Ser. No. 893,766 for Atomic Absorption Spectrometer filed Aug. 6, 1986 so that the burner flame is selectively movable between positions within and without the single measuring beam path.

The burner head 14 is rotatably mounted with a cylindrical socket 46 in an annular supporting element 22. The supporting element 22 is connected to the mixing chamber 12 by a cap nut 24. The mixing chamber 12 has a collar 26 with an outer thread 28. The cap nut 24 has a knurled handle portion 30 of relatively large diameter, an intermediate radial annular portion 32 having apertures 34 and an internally threaded portion 36 which is threadably fastened to the collar 26. A rim 38 of the cap nut 24 overlaps an outer flange 40 of the bearing element 22. The collar 26 forms a shoulder 42 on its inner side and an O-ring 44 lies on the shoulder 42. The bearing element 22 lies with one end face on the O-ring 44.

Figure 2:
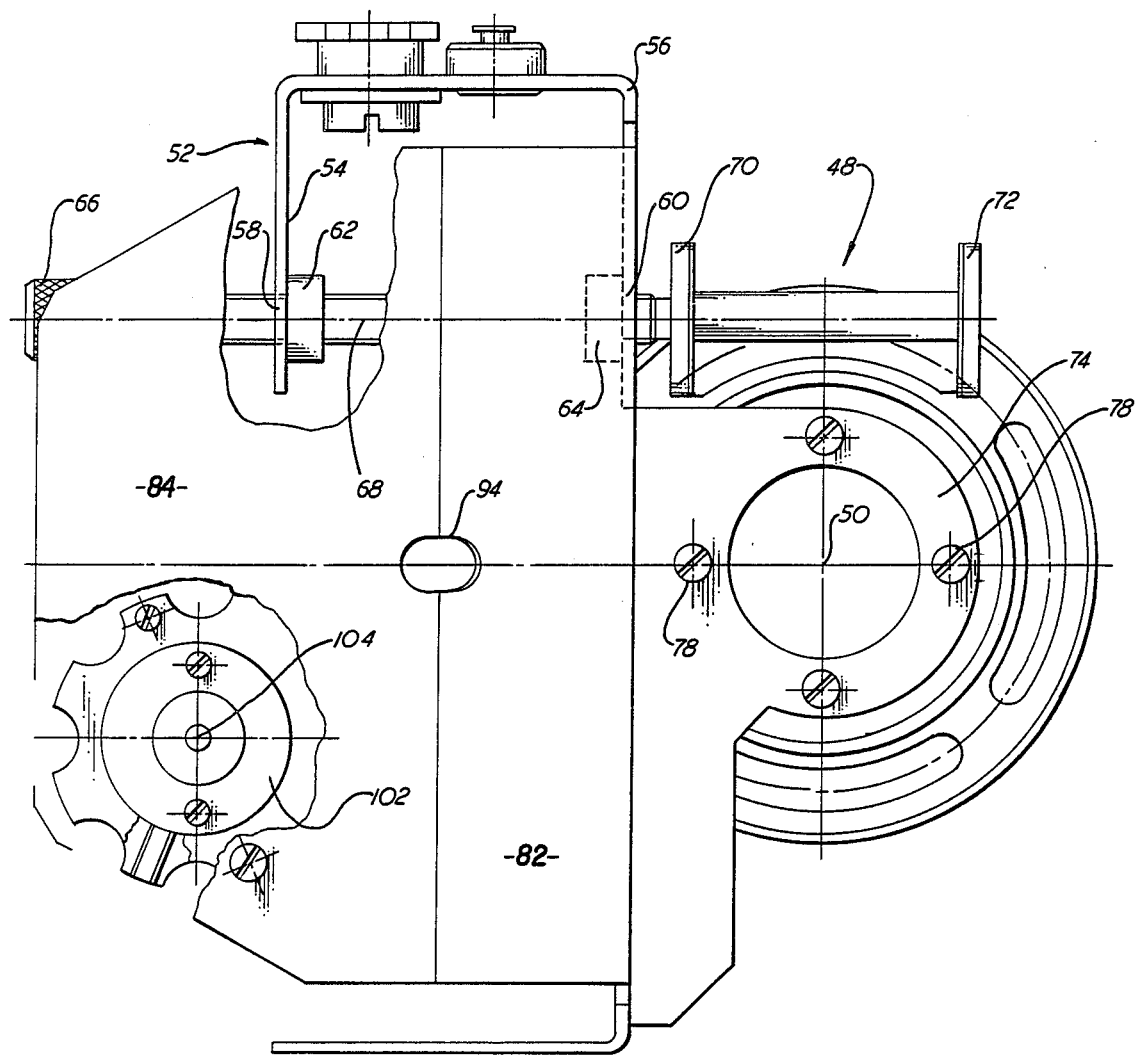
FIG. 2 is a diagrammatic plan view, partially broken away, of the burner assembly of FIG. 1.

Referring to FIG. 2, an acting device 48 is mounted on the carrier 20 so as to engage the burner head 14 outside the axis 50 of the socket 46 for limited angular adjustment between the burner head 14 and the bearing portion 22 and a carrier 20, respectively. The burner head 14 is oblong in a longitudinally direction (perpendicular to the plane of the paper in FIG. 1). A U-shaped bracket 52 is formed on the carrier 20 by bending with two bracket legs 54 and 56 extending substantially parallel to the longitudinal direction of the burner head 14. The legs 54 and 56 have aligned apertures 58, 60 mounting threaded nuts 62 and 64, respectively. An actuating spindle 68 rotatable by an actuating knob 66 is guided in the threaded nuts 62 and 64. The actuating spindle 68 extends below the burner head 14 (not visible in FIG. 2) and has flanges 70 and 72, respectively, which engage the burner head 14 on opposite sides. The burner head is rotatable about the axis 50 through a limited angle relative to the bearing portion 22 and carrier 20 by the actuating device 48 engaging the burner head 14 outside the axis 50. Apart from the actuating movement however, the burner head 14 is precisely and fixedly connected to the bearing portion 22 and the carrier 20.

The carrier or support plate 20 is a unitary sheet metal element produced from a single sheet metal cut by bending, stamping and the like and, for purposes of description, comprises bent or deflected sections 74, 80, 82 and 84. The carrier 20 is affixed to the bearing portion 22 as follows. The carrier 20 has a deflected section 74 extending horizontally with an aperture 76. The socket 46 of the burner head 14 extends through the aperture 76. The section 74 is securely connected to the front or upper side of the bearing portion 22 by screws 78 which are arranged around the aperture 76. The carrier section 80 adjoins section 74 and extends perpendicularly upwardly to adjoining section 82. Section 82 extends at an angle upwardly away from the burner head 14 and adjoins the horizontally extending section 84.

A block or support housing 86 consisting of material exhibiting low heat conduction properties is mounted below the horizontally extending section 84. The block 86 has a bore 90 extending at an angle to the burner head 14 with the axis 92 of the bore 90 being directed to a point above the burner head 14. The carrier 20 contains an aperture of 94 in alignment with the axis 92 of bore 90 to permit monitoring of the burner head flame. The flame sensor 18 comprises a sensor element 96 in the form of a thermo-column mounted in the bore 90 so as to respond to the heat radiation of the flame.

The thermo-column 96 is exposed to heat radiation of the flame through the aperture 94. This radiation impinges upon the desired portions of the thermo-column for generation of a corresponding electrical signal. The remaining portions of the thermo-column however are screened against direct heat radiation of the flame by the carrier 20 and additional insulation. By this arrangement, monitoring by the thermocolumn is limited to the area immediately at the burner head.

The block 86 also has a substantially vertical bore 100 mounting a rotary magnet 102. The armature of the magnet 102 is movable about a vertical axis 104 between first and second positions. An ignition 106 of the type shown in the commonly assigned Huber et al., U.S. patent application filed Sept. 10, 1986 entitled Device and Technique for Igniting a Flame In An Atomic Absorption Spectrophotometer is mounted for pivotal movement by the rotary magnet 102. The free end of the tube 106 remote from the rotary magnet 102 is cut off at an angle so that an opening is formed facing downwardly to facilitate the entry and conduction of fuel gas from the burner head, 14. In a first operational position, the free end of the tube 106 is disposed above the burner head 14 so as to receive fuel gas from the burner head 14. In the second inoperative position, the free end of the tube 106 is located outside the region of the burner head 14.

The tube 106 has an opening 108 at the underside of the end facing the rotary magnet 102. A glow means in the form of a glow plug 110 is mounted below the opening 108 for igniting the fuel gas. The tube 106 is supported in a head member 112 which is connected to the armature of the rotary magnet 102 in a manner permitting adjustment in level. Two stationary stop means opposite each other (not shown) are provided between rotary magnet 102 and head portion 112. A resilient, preferably rubber-like abutment body 118 is mounted on the head portion 112 extending between these stationary stop means so that the first and second positions respectively of the rotary magnet 102 are determined by the stationary stop means and the abutment body 118.

Figure 3:
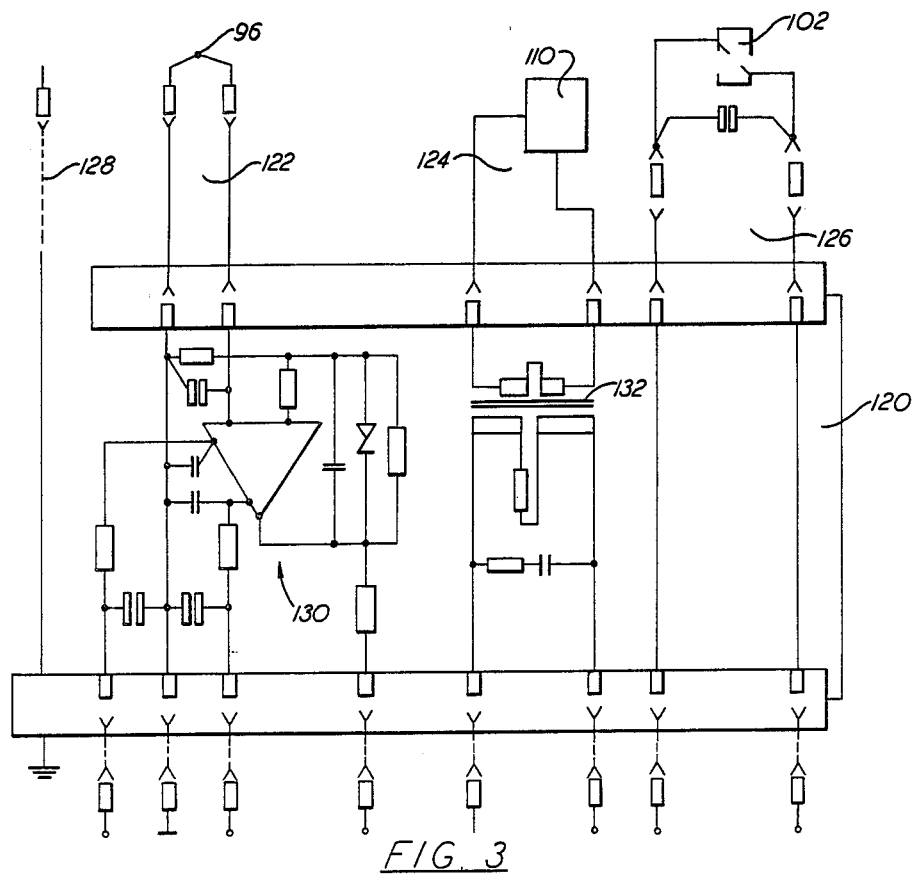
FIG. 3 is a circuit diagram of the burner assembly of FIG. 1.

Referring to FIG. 3 wherein the associated electronic circuit is shown, the numeral 120 designates a printed circuit board to which the thermo column 96 (illustrated as a thermo element), the glow plug 110, and the rotary magnet 102 are connected by conductors 122, 124, and 126 respectively. The conductor 122 and the thermo column 96 are screened by a grounded screening 128. The signal of the thermo column 96 is amplified by a conventional amplifier 130 of the type having a low noise component and which need not be described in detail. The sensor signal is used to control the valves for the gas supply to the burner. The glow plug 110 is connected to a power supply through a transformer 132 attached to the printed circuit board 120. The rotary magnet is connected to a control apparatus which is arranged to activate the pivotal movement of the tube 106 into the area of the burner head 14 and to simultaneously energize the glow plug 110.

The cap nut 124 is configured so that it can be touched by hand when the flame is burning. To limit the temperature of the cap nut 24, the radial ring portion has apertures 34 allowing a circulation of air to reduce the resistance of the heat transfer to the corrugated ring 30. Therefore, if necessary, the cap nut 24 can be loosened slightly while the flame is burning. Then it is possible to touch the block 86 and to rotate the whole carrier with the bearing ring 22 and the burner head 14.

As will be apparent to persons skilled in the art, various modifications and adaptations of the structure above described will become readily apparent without departure from the spirit and scope of the invention, the scope of which is defined in the appended claims.

What is claimed is:

1. A burner assembly for an atomic absorption spectrometer defining a predetermined optical path for a measuring light beam comprising
    burner means for generating a flame for atomization of a sample to be analyzed, said burner means having a burner head for connection to a source of fuel gas and being movably mounted for selective movement relative to said optical path, said burner means forming a mixing chamber and having an annular support element mounting said burner head and threaded connection means for detachably connecting said annular support element to said mixing chamber, said annular support element being connected to said mixing chamber,
    a support carrier securely connected to said burner means, said carrier being a unitary plate element securely connected to said annular support element,
    ignition means for igniting a flame on said burner head, said ignition means being mounted on said carrier, and
    sensor means for monitoring a flame on said burner head, said sensor means being positioned in predetermined alignment with said burner means and securely mounted to said carrier so as to maintain said alignment after selective movement of said burner means.

2. The device of claim 1 wherein said ignition means is positioned in predetermined operational alignment with said burner means and securely mounted to said carrier so as to maintain said alignment after selective movement of said burner means.

3. The device of claim 1 wherein said burner means is movably mounted for selective movement within said optical path.

4. A burner assembly for an atomic absorption spectrometer defining a predetermined optical path for a measuring light beam comprising
    burner means for generating a flame for atomization of a sample to be analyzed, said burner means having a burner head for connection to a source of fuel gas and being movably mounted for selective movement relative to said optical path, said burner head having a cylindrical socket, said burner means forming a mixing chamber and having an annular support element, said burner head being rotatably mounted with said socket in said annular support element, means for detachably connecting said annular support element to said mixing chamber, said annular support element being connected to said mixing chamber, and actuating means for selectively rotating said burner head for angular adjustment between said burner head and said annular supporting element,
    a support carrier securely connected to said annular support element,
    ignition means for igniting a flame on said burner head, said ignition means being mounted on said carrier, and
    sensor means for monitoring a flame on said burner head, said sensor means being positioned in predetermined alignment with said burner means and securely mounted to said carrier so as to maintain said alignment after selective movement of said burner means.

5. The device of claim 4 wherein said ignition means is positioned in predetermined operation alignment with said burner means and securely mounted to said carrier so as to maintain said alignment after selective movement of said burner means.

6. The device of claim 4 wherein said carrier is a unitary plate element connected to said burner head.

7. The device of claim 4 wherein said carrier is a unitary plate element, said burner head is elongated in a longitudinal direction, and said actuating means comprises
    a u-shaped bracket integrally formed on said carrier with spaced legsextending generally parallel to the longitudinal direction of said burner head, said legs having aligned threaded guide apertures, and
    a rotatable actuating spindle mounted within said guide apertures and having a knob at one end for rotating said spindle and two flanges at said other end in engagement with said burner head for angular adjustment of said burner head by rotation of said spindle.

8. The device of claim 4 wherein said carrier comprises a horizontally disposed deflected portion with an aperture, said socket of said burner head extending through said aperture, and said first portion being securely connected to said support element by threaded fasteners disposed about said aperture.

9. A burner assembly for an atomic absorption spectrometer defining a predetermined optical path for a measuring light beam comprising
    burner means for generating a flame for atomization of a sample to be analyzed, said burner means having a burner head for connection to a source of fuel gas and being movably mounted for selective movement relative to said optical path, said burner head having a cylindrical socket, said burner means forming a mixing chamber and having an annular support element mounting said burner head, and means for detachably connecting said annular support element to said mixing chamber, a support carrier securely connected to said burner means, said carrier being a unitary plate element and having a horizontally disposed deflected first portion with an aperture, said first carrier portion being securely connected to said annular support element with said burner head socket extending through said aperture, ignition means for igniting a flame on said burner head, said ignition means being mounted on said carrier, and sensor means for monitoring a flame on said burner head, said sensor means being positioned in predetermined alignment with said burner means and securely mounted to said carrier so as to maintain said alignment after selective movement of said burner means.

10. The device of claim 9 wherein said ignition means is positioned in predetermined operation alignment with said burner means and securely mounted to said carrier so as to maintain said alignment after selective movement of said burner means.

11. The device of claim 9 which comprises said carrier having a second deflected portion extending upwardly from said first portion at an angle away from said burner head, said second section extending between said flame sensor means and said burner head and having an aperture aligned for passage of radiation from the burner flame to said flame sensor means.

12. The device of claim 9 which comprises said carrier having a second deflected portion extending upwardly from said first portion at an angle away from said burner head and a horizontally disposed third portion adjoining said second portion, a support housing formed of low heat-inductance material mounted below said third carrier portion and having a bore extending at an angle with respect to said burner head such that the longitudinal axis of the bore is aligned above said burner head at the position of the burner flame, said second carrier portion being disposed between said support housing and said burner head and having an aperture in alignment with the axis of said bore, and said flame sensor means having a sensor element mounted within said bore.

13. The device of claim 12 wherein said sensor element is a thermo-column.

14. A burner assembly for an atomic absorption spectrometer defining a predetermined optical path for a measuring light beam comprising burner means for generating a flame for atomization of a sample to be analyzed, said burner means having a burner head for connection to a source of fuel gas and being movably mounted for selective movement relative to said optical path, a support carrier securely connected to said burner means, ignition means for igniting a flame on said burner head, said ignition means being mounted on said carrier, and sensor means for monitoring a flame on said burner head, said sensor means being positioned in predetermined alignment with said burner means and securely mounted to said carrier so as to maintain said alignment after selective movement of said burner means, said ignition means comprising a gas conducting body having a first end adapted to be positioned adjacent said burner head to receive a portion of fuel gas from said burner head and conduct it to a second outlet end remote from said burner head for ignition by a glow filament means for igniting gas to thereby ignite the burner head, means for movably mounting said gas conducting body on said carrier for movement between first and second positions with said first end being adjacent said burner head to receive fuel gas in said first position and remote from said burner head to prevent gas flow therethrough in said second position, and glow filament means for igniting gas mounted adjacent said second end of said gas conducting body.

15. The device of claim 14 wherein said carrier is a unitary plate element connected to said burner head.

16. The device of claim 12 which comprises said carrier having a horizontally disposed first portion with an aperture mounting said burner head, a second portion extending upwardly from said first portion at an angle away from said burner head and a horizontally disposed third portion, said means for mounting said gas conducting body being mounted to said third portion, and said sensor means being mounted to said carrier below said third portion with said second portion having an aperture for passage of radiation from said burner head to said sensor means.

17. The device of claim 16 which comprises a support housing mounted below said third carrier portion having a substantially vertical bore, and a rotary magnet actuator mounted within said bore for rotation about a vertical axis between first and second positions, said gas conducting body being mounted to said magnetic actuator for actuation between said first and second positions.

18. The device of claim 17 wherein said support housing is formed of low heat-conductive material and has a second bore extending at an angle with espect to said burner head such that the longitudinal axis of the bore is aligned above said burner head at the position of the burner flame, said second carrier portion being disposed between said support housing and said burner head with an aperture in alignment with the axis of said second bore, and said flame sensor means having a sensor element mounted within said second bore.

19. A burner assembly for an atomic absorption spectrometer defining a predetermined optical path for a measuring light beam comprising burner means for generating a flame for atomization of a sample to be analyzed, said burner means having a burner head for connection to a source of fuel gas and being movably mounted for selective movement relative to said optical path, a support carrier securely connected to said burner means, ignition means for igniting a flame on said burner head, said ignition means being mounted on said carrier, and sensor means for monitoring a flame on said burner head, said sensor means being positioned in predetermined alignment with said burner means and securely mounted to said carrier so as to maintain said alignment after selective movement of said burner means, said carrier having a horizontally disposed first portion mounting said burner head, a second portion extending upwardly away from said first portion at an angle, and a horizontally disposed third portion, said carrier having upper and lower surfaces, said sensor means being mounted to said third portion and disposed below said carrier such that said second portion is positioned between said sensor means and said burner head, and said second portion having an aperture in alignment with said sensor means and the position of a flame on said burner head for the passage of radiation from said flame to said sensor means.

20. The device of claim 19 wherein said ignition means is positioned in predetermined operational alignment with said burner means and securely mounted to said carrier so as to maintain said alignment after selective movement of said burner means.

21. The device of claim 19 wherein said carrier is a unitary plate element connected to said burner head.

22. The device of claim 19 wherein said sensor means comprises a thermocolumn.

* * * * *